United States Patent [19]

Lartey et al.

[11] 4,242,503
[45] Dec. 30, 1980

[54] PROCESS FOR O-DEMETHYLATING FORTIMICINS

[75] Inventors: Paul A. Lartey, Waukegan; David J. Grampovnik, North Chicago, both of Ill.

[73] Assignee: Abbott Laboratories, North Chicago, Ill.

[21] Appl. No.: 25,237

[22] Filed: Mar. 29, 1979

[51] Int. Cl.$^3$ .............................................. C07H 15/22
[52] U.S. Cl. ..................................... 536/17 R; 536/4; 568/907
[58] Field of Search ......................... 536/17 R, 1, 120; 568/907

[56] References Cited

U.S. PATENT DOCUMENTS 4,124,756   11/1978   Martin et al. ........................... 536/17

OTHER PUBLICATIONS

Pigman, "The Carbohydrates", 1957, Academic Press, Inc., New York, N.Y., p. 368.
Noller, "Chemistry of Organic Compounds", 1965, W. B. Saunders Co., Philadelphia, Pa. pp. 161, 395 and 846.

Primary Examiner—Johnnie R. Brown
Attorney, Agent, or Firm—Robert L. Niblack; Gildo E. Fato; Joyce R. Niblack

[57] ABSTRACT

Described is a method of O-demethylating a fortimicin compound using hydriodic acid or tri-methylsilyiodide as an O-demethylating agent.

9 Claims, No Drawings

PROCESS FOR O-DEMETHYLATING FORTIMICINS

BACKGROUND OF THE INVENTION

The aminoglycoside antibiotics are a valuable therapeutic class of antibiotics which include the kanamycins, gentamicins, streptomycins and the more recently discovered fortimicins. While the naturally produced parent antibiotics are, in themselves valuable entities, chemical modifications have been found to improve the activity, either intrinsic activity or activity against resistant strains, or reduce the toxicity of the parent antibiotics. And, because of the development of aminoglycoside resistant strains and inactivation of the parent antibiotics by R-mediated factors which can develop, the search for new entities continues.

One such entity has been discovered in the fortimicin family of antibiotics, 3-O-demethylfortimicin A. 3-O-demethylfortimicin B is also of interest because of its usefulness in preparing fortimicin derivatives. The 3-O-demethylfortimicins are disclosed in U.S. Pat. No. 4,124,756, issued November 7, 1979.

Previously known methods for producing O-demethylfortimicins have resulted in inefficient, slow synthesis and resulted in yields that are not satisfactory for commercial production, although satisfactory for laboratory synthesis. Thus there has been a need for improved processes to improve the yield of 3-O-demethylfortimicin production. The present invention provides one such method.

SUMMARY

The present invention provides an improved process for O-demethylating a fortimicin antibiotic comprising the steps of reacting a fortimicin to be O-demethylated with a compound selected from the group consisting of hydriodic acid or trimethylsilyliodide and isolating the O-demethylated fortimicin from the reaction mixture.

DETAILED DESCRIPTION OF PREFERRED EMBODIMENTS

For illustrative purposes, the invention will be exemplified by the O-demethylation of fortimicin A and fortimicin B. However, its application extends to the O-demethylation of derivatives of fortimicin A and B and to other fortimicins as well.

Generally speaking, in the practice of this invention, if the fortimicin is to be O-demethylated with hydriodic acid, the compound is treated with hydriodic acid, preferably 48% hydriodic acid, in aqueous solution. The reaction is commenced at room temperature and the temperature gradually raised to from about 50° to about 70° and preferably 60° C. over a period of from about 30 minutes to about 4 hours, preferably 2 hours, and thereafter, the reaction mixture is maintained at the higher temperature, preferably with continued stirring from about 16 to about 24 and preferably about 18 hours. Thereafter, the O-demethylated fortimicin is recovered from the reaction mixture by ion exchange techniques.

When hydriodic acid is employed, it is preferred to employ 100 ml of 48% hydriodic acid per gram of fortimicin to be O-demethylated. However, from about 10 to about 100 ml of acid for each gram of fortimicin to be O-demethylated can be employed in the practice of this invention.

When trimethylsilyliodide is used, it is preferred to employ from about 3 to about 6 and preferably about 4 ml of trimethylsilyliodide per gram of antibiotic to be O-demethylated. In the case of O-demethylation with trimethylsilyliodide, the fortimicin antibiotic is first dissolved in a suitable inert organic solvent such as chloroform or methylene chloride. The reaction is carried out at from about 50° to about 60° C., preferably 55° C., preferably under a nitrogen atmosphere for at least 12 and preferably up to 24 hours, and the O-demethylated fortimicin is recovered from the reaction mixture, preferably by silica gel chromatography.

The following examples further illustrate the present invention.

EXAMPLE I

3-O-Demethylfortimicin B

Fortimicin B (1 g, 2.86 mmole) was dissolved in 100 ml of 48% hydriodic acid at room temperature. The solution was stirred and the temperature raised to 60° C. over a period of 2 hours. Stirring was continued for a further 18 hours at 60° C. The solution was allowed to cool to room temperature and diluted with 100 ml of water. The solution was passed through a column (1.5 l.) of "Amberlite" IRC-50 cation exchange resin in the ammonium form. The resin was washed with water until the washings gave a negative test for iodide with silver nitrate solution. Gradient elution with one l. of 1 M ammonium hydroxide into 1 l. of water afforded 3-O-demethyl fortimicin B in 30% yield.

EXAMPLE II

3-O-Demethylfortimicin A

Fortimicin A sulfate (1.48 g, 2.46 mmole) was dissolved in 160 ml of 48% hydriodic acid at room temperature. The solution was stirred and the temperature gradually raised to 62° C. Stirring was continued at 62° C. for 20 hours. The solution was diluted with 160 ml of water and passed through a 1.5 l. column of "Amberlite" IRC-50 in the ammonium form. The column was washed with water and eluted with an ammonium hydroxide gradient as described in Example 1 resulting in the recovery of 3-O-demethylfortimicin A in 25% yield.

EXAMPLE III

3-O-demethylfortimicin B

Fortimicin B (0.507 g, 1.43 mmole) was dissolved in 10 ml of dry chloroform. Trimethylsilyliodide (1.6 ml, 10.04 mmole) was added under a nitrogen atmosphere. The mixture was stirred and warmed up to 55°. Stirring was continued at 55° and under nitrogen for 24 hours. The mixture was cooled to room temperature, filtered and the filtrate extracted four times with 15 ml portions of water. The aqueous extracts were combined and water removed in vacuo. The residue was chromatographed over a silica gel column, using a solvent system of 1,2-dichloroethane, methanol and ammonium hydroxide (3:2:1 ratio). A 10% yield of 3-O-demethylfortimicin B was obtained.

We claim:

1. A process for O-demethylating a fortimicin comprising the steps of reacting the fortimicin to be O-demethylated with a compound selected from the group consisting of hydriodic acid and trimethylsilyliodide, said reaction being commenced at room temperature and the temperature being gradually raised to a temperature of from 50° to 70° C. over a period of from 30 minutes to four hours, and thereafter maintaining said reaction mixture at said higher temperature for a period of from 12 to 24 hours until hydrolysis of the 3-O-methyl substituent is completed and thereafter removing said O-demethylated fortimicin from the reaction mixture.

2. The method of claim 1 wherein said compound is hydriodic acid.

3. The method of claim 2 wherein said hydriodic acid is 48% hydriodic acid.

4. The method of claim 1, 2 or 3 wherein said raised temperature is 60° C.

5. The method of claim 4 wherein from about 10 to 100 ml of hydriodic acid per gram of fortimicin is reacted.

6. A process for O-demethylating a fortimicin comprising the steps of reacting the fortimicin to be O-demethylated with trimethylsilyliodide, said reaction being commenced at room temperature and the temperature being gradually raised to a temperature of from 50° to 70° C. over a period of from 30 minutes to four hours, and thereafter maintaining said reaction mixture at said higher temperature for a period of from 12 to 24 hours until hydrolysis of the 3-O-methyl substituent is completed and thereafter recovering said O-demethylated fortimicin from the reaction mixture.

7. The method of claim 6 wherein said fortimicin is first dissolved in an inert organic solvent.

8. The method of claim 7 wherein from about 3 to about 6 ml of trimethylsilyliodide are reacted with each gram of fortimicin to be O-demethylated.

9. The method of claim 6 wherein said reaction is carried out at a temperature of from 50° to 60° for from 12 to 24 hours.

* * * * *